(12) United States Patent
Garde et al.

(10) Patent No.: US 9,156,002 B2
(45) Date of Patent: Oct. 13, 2015

(54) PROCESS FOR CONTROLLING THE PH AND LEVEL OF TARGET IONS OF A LIQUID COMPOSITION

(75) Inventors: Arvid Garde, HillerØd (DK); Jens-Ulrik Rype, Gentofte (DK)

(73) Assignee: CARLSBERG A/S, Kobenhavn V (DK)

( * ) Notice: Subject to any disclaimer, the term of this patent is extended or adjusted under 35 U.S.C. 154(b) by 367 days.

(21) Appl. No.: 13/062,772

(22) PCT Filed: Sep. 4, 2009

(86) PCT No.: PCT/EP2009/006440
§ 371 (c)(1), (2), (4) Date: May 25, 2011

(87) PCT Pub. No.: WO2010/025935
PCT Pub. Date: Mar. 11, 2010

(65) Prior Publication Data
US 2011/0215000 A1    Sep. 8, 2011

Related U.S. Application Data

(60) Provisional application No. 61/095,124, filed on Sep. 8, 2008.

(30) Foreign Application Priority Data

Sep. 8, 2008    (EP) ................................. 08163855

(51) Int. Cl.
*B01D 61/44* (2006.01)
*B01D 61/58* (2006.01)
*B01D 61/52* (2006.01)
*B01D 61/54* (2006.01)
*B01D 61/42* (2006.01)
*C12P 7/56* (2006.01)
*C12M 1/00* (2006.01)
*B01D 61/14* (2006.01)

(52) U.S. Cl.
CPC .............. *B01D 61/52* (2013.01); *B01D 61/422* (2013.01); *B01D 61/44* (2013.01); *B01D 61/58* (2013.01);

(Continued)

(58) Field of Classification Search
CPC ........................................................ C12M 21/00
USPC ..................................... 204/522, 630; 435/41
See application file for complete search history.

(56) References Cited

U.S. PATENT DOCUMENTS 3,369,906 A * 2/1968 Chen ............................ 426/239
4,882,277 A   11/1989 Czytko et al.

(Continued)

FOREIGN PATENT DOCUMENTS

GB        1037725       8/1966
JP    S 62-146595 A    6/1987

(Continued)

OTHER PUBLICATIONS

Rype et al., "Combining membrane separation and fermentation processes for improved performance", European Congress of Chemical Engineering (ECEE-6) (Sep. 16-20, 2007) Copenhagen.

*Primary Examiner* — Keith Hendricks
*Assistant Examiner* — Salil Jain
(74) *Attorney, Agent, or Firm* — Novak Druce Connolly Bove + Quigg LLP (57) ABSTRACT

A process for simultaneously controlling the pH and level of target ions of a liquid composition, more particularly the use of Reverse Electro-Enhanced Dialysis (REED) for extraction of low-molecular, charged species generated in a reactor. Even more particularly, the invention relates to a process for simultaneous pH control and control of inhibitors in an ongoing fermentation or catalytical system, where the pH is controlled by at least one primary Reverse Electro-Enhanced Dialysis (REED) stack and the level of target ions by at least one secondary REED stack, where the primary REED is one of a Cation REED (CX-REED) or an Anion REED (AX-REED) and the secondary REED is the other of a CX-REED and an AX-REED.

20 Claims, 6 Drawing Sheets (52) U.S. Cl.
CPC ............ *B01D 61/145* (2013.01); *B01D 61/147* (2013.01); *B01D 2311/12* (2013.01); *B01D 2311/2688* (2013.01); *B01D 2317/02* (2013.01); *B01D 2317/04* (2013.01); *B01D 2317/08* (2013.01); *C12M 21/00* (2013.01); *C12P 7/56* (2013.01)

(56) References Cited

U.S. PATENT DOCUMENTS

| | | | |
|---|---|---|---|
| 4,921,792 A * | 5/1990 | Trawinski et al. | 435/41 |
| 5,114,554 A | 5/1992 | Voss et al. | |
| 5,547,542 A * | 8/1996 | Landfors | 162/29 |
| 5,736,023 A | 4/1998 | Gallagher et al. | |
| 5,746,920 A | 5/1998 | Boergardts et al. | |
| 5,747,306 A | 5/1998 | Oka et al. | |
| 7,358,067 B2 * | 4/2008 | Vrang et al. | 435/69.8 |
| 7,704,361 B2 * | 4/2010 | Garde et al. | 204/522 |
| 8,961,769 B2 | 2/2015 | Garde et al. | |
| 2006/0094093 A1 * | 5/2006 | Carlson et al. | 435/139 |
| 2007/0215474 A1 * | 9/2007 | Batchelder et al. | 204/524 |

FOREIGN PATENT DOCUMENTS

| | | |
|---|---|---|
| JP | S 63-148979 | 6/1988 |
| JP | H 7-67673 | 3/1995 |
| JP | 2007-509747 | 4/2007 |
| WO | WO01/21538 A1 | 3/2001 |
| WO | WO02/48044 | 6/2002 |
| WO | WO 2005/044427 | 5/2005 |

* cited by examiner

PROCESS FOR CONTROLLING THE PH AND LEVEL OF TARGET IONS OF A LIQUID COMPOSITION

CROSS REFERENCE TO RELATED APPLICATIONS

This application is a §371 national phase entry of International Application No. PCT/EP2009/006440, filed Sep. 4, 2009, which claims priority to European Application No. 08163855,3, filed Sep. 8, 2008, and U.S. Provisional Patent Application No, 61/095,124, filed Sep. 8, 2008, the entire contents of which are incorporated herein by reference.

FIELD OF THE INVENTION

The present invention relates to a process for controlling the pH and level of target ions of a liquid composition. More particularly the invention concerns the use of Reverse Electro-Enhanced Dialysis (REED) for extraction of low-molecular, charged species generated in a reactor. Even more particularly the invention relates to a process for pH control and control of inhibitors in bioreactors.

BACKGROUND OF THE INVENTION

Controlling the pH and/or level of target ions of a liquid composition is an important industrial process used within such broad technical fields as metal refining and purification of organic substances from a fermented liquid.

A number of processes have been introduced in order to control the pH and/or level of target ions of a liquid composition. Among said processes are micro- and ultrafiltration processes, ion-exchange processes and electrodialysis processes.

E.g. bioreactors are used extensively in the industry for production of a wide range of organic chemicals, pharmaceutical proteins, amino acids, starter cultures, biofuels etc., or for biodegradation purposes. Most often, the bioreactor contains microorganisms that require a certain pH level to sustain optimal functionality.

Standard means for pH regulation in bioreactors includes titration of alkaline or acidic neutraliser directly into the bioreactor, to neutralize acidic or alkaline metabolites produced by the microorganisms. However, salts of these metabolites often inhibit growth when reaching a certain concentration.

The build-up of some salts and metabolites, such as inhibitors for biological reactions, sets a limit to the productivity of a bioreactor in normal batch operations. Possible solutions to minimize inhibition include perfusion systems, where fermentation broth with inhibitors is continuously extracted through a filter process (e.g. ultra- or microfiltration), while retaining the microorganisms and adding fresh substrate solution to the fermenter. In perfusion systems, it is still necessary to regulate bioreactor pH through titration of neutralizer and valuable substrate components are lost with the permeate.

The use of ion-exchange membranes, as utilized in electrodialysis and the so-called Donnan Dialysis processes, allows for a more selective extraction of small charged species compared to membranes typically used in ultra- and microfiltration. However, conventional electrodialysis suffers from membrane fouling when combined directly with bioreactors and neutralizer titration is still necessary for pH control.

EP patent 1 237 823 discloses an apparatus and a method for transferring ionic species from a first liquid to a second liquid in an electro-enhanced dialysis cell comprising either cation exchange membranes or anion exchange membranes.

U.S. Pat. No. 5,114,554 discloses a process for removing acid from a cathodic electrocoating bath in which electroconductive substrates are being coated with cationic resins, at least a portion of the coating bath being subjected to an ultrafiltration, and at least a portion of the ultrafiltrate being subjected to a specific electrodialysis treatment in a direct current operated electrodialysis cell comprising anion exchange membranes.

SUMMARY OF THE INVENTION

There is a need for a process for controlling both the pH and the level of target ions of a liquid composition, which process allows a more precise control of pH without direct addition of chemicals and which process allows controlling the level of target ions independently of the desired pH set-point.

Thus in a first aspect the present invention relates to a process for controlling the pH and level of target ions of a liquid composition comprising the steps of, in either order:
a) at least one step of passing said liquid through at least one Reverse Electro-Enhanced Dialysis (REED) membrane stack having:
  i) at least two ion-exchange membranes defining a first chamber for a first liquid there between;
  ii) at least two further chambers for a second liquid, each further chamber being located adjacent to the at least one first chamber;
  iii) a set of end membranes; and
  iv) means for applying an electric field over the membranes by means of at least two electrodes; and
b) at least one step of controlling the level of target ions in said liquid.

A second aspect of the invention is a system comprising:
a) at least one Anion Exchange Reverse Electro-Enhanced Dialysis (AX-REED) membrane stack having:
  i. at least two Anion-exchange membranes defining a first chamber for a first liquid there between;
  ii. at least two further chambers for a second liquid, each further chamber being located adjacent to at least one first chamber;
  iii. a set of end membranes; and
  iv. means for applying an electric field over the membranes by means of at least two electrodes; and
b) at least one Cation Exchange Reverse Electro-Enhanced Dialysis (CX-REED) membrane stack having
  v. at least two Cation-exchange membranes defining a third chamber for a third liquid there between;
  vi. at least two further chambers for a fourth liquid, each further chamber being located adjacent to the at least one third chamber;
  vii. a set of end membranes; and
  viii. means for applying an electric field over the membranes by means of at least two electrodes;
wherein said at least one Anion Exchange Reverse Electro-Enhanced Dialysis (AX-REED) membrane stack and said at least one Cation Exchange Reverse Electro-Enhanced Dialysis (CX-REED) membrane stack are in serial or parallel connection.

A third aspect of the invention is the use of a system according to the invention for controlling the pH and level of target ions of a liquid composition.

Other aspects of the invention will become apparent to the person skilled in the art from the following detailed description and examples.

DEFINITIONS

In the context of this invention the term "target ion(s)" is meant to encompass both unwanted ions, e.g. inhibitors in a fermentation process, and ions constituting a desired product being removed from the liquid composition. As a non-limiting example of a target ion may be mentioned the lactate ion. Lactic acid is a known inhibitor for Lactic Acid Bacteria (LAB) cultures, and thus, for bioreactors with live LAB cultures, lactate could be a target ion for the REED process. The term "target ions" does not encompass hydrogen ions.

In the context of this invention the term "Reverse Electro-Enhanced Dialysis" or "REED" covers both AX-REED and CX-REED.

In the context of this invention the term "AX-REED" means a REED setup where Anion-exchange membranes are used as barrier between feed solution and dialysate and exchange of anions between the two liquids is facilitated.

In the context of this invention the term "CX-REED" means a REED setup where Cation-exchange membranes are used as barrier between feed solution and dialysate and exchange of cations between the two liquids is facilitated.

In the context of this invention the term "stack" means a unit of a REED system comprising one or more repeating sets of a combination of at least two ion-exchange membranes, a set of end membranes and at least two electrodes surrounding said membranes.

In the context of this invention the term "multiple REED membrane stacks" means two or more stacks of membranes and spacers, each stack placed between a pair of electrodes.

In the context of this invention the term "reversal of the electric field" or "current reversal" means the changing of polarity of the REED electrodes, resulting in a reversal of the direction of the electrical DC current, which facilitates the migration of ions through the ion-exchange membranes.

In the context of this invention the term "control" or "controlling" means the ability, manually or automatically to adjust the desired parameter, e.g. concentration of target ions, using REED and/or titration and/or water addition.

BRIEF DESCRIPTION OF THE DRAWINGS

The invention is disclosed with reference to the drawings, wherein.

DETAILED DESCRIPTION OF THE INVENTION

REED Principle

The Reverse Electro-Enhanced Dialysis (REED) process utilizes ion-exchange membranes in a plate-and-frame membrane setup similar to the so-called Donnan Dialysis setup, the latter utilizing diffusion caused by a difference in chemicals potentials as the driving force. However, in the REED process the exchange of ions is boosted and regulated by an electrical DC current across the membrane setup. The REED process is intended for use on process solutions entailing components too large to penetrate the membranes (e.g. proteins), which tend to collect on the surface of ion-exchange membranes; this effect is known as membrane fouling. By utilizing the REED process's symmetrical setup, the direction of the electrical current can be reversed at regular intervals without significant interference in the separation process.

Typically, a process solution (feed solution) flows through a REED system, where either negatively charged ions (anions) are exchanged for other anions, thus named an Anion Exchange REED setup (AX-REED), or positively charged ions (cations) are exchanged for other cations in a Cation Exchange REED setup (CX-REED). A dialysate solution carries the ions, which are exchanged for the ions in the feed solution. In a plate-and-frame setup, several membranes are stacked, separated by flow spacers facilitating alternately the feed and the dialysate solutions, respectively. In an embodiment of the invention the polarity of said at least two electrodes is changed at intervals.

During the separation, the two membranes surrounding each feed spacer compartment either facilitates the transport of ions out of the feed solution or into the feed solution from the dialysate.

Each reversal of the direction of the electric field/electrical current results in a short-term reestablishment of the affected ions' polarization profiles through the membranes, as the two membranes surrounding each feed compartment exchanges functions. This causes a short-term reversal of the separation process as the ions previously being removed are pushed back into the feed solution until the membrane profiles are re-established. It is advantageous to keep the intervals between current reversals as long as allowed by the build-up of fouling, as each reversal introduces a short separation pause and introduces minor process instability.

In an embodiment of the invention multiple REED stacks are operated in parallel. Such set-up minimizes e.g. the impact on microorganisms in a bioreactor as the holding time outside the bioreactor as well as the pH deviation from the set point is reduced compared to operation in series.

In another embodiment of the invention multiple REED stacks are operated in series or cascade. Such set-up allows for higher removal of ions per pass and is better suited for continuous downstream operations.

The REED process may be used for extracting inhibitors like organic acid ions from bioreactors/live fermentation processes to improve productivity and longevity of cell growth (continuous fermentation) and/or to regulate metabolite production (e.g. recombinant protein). The REED process may e.g. be used for pH control in biological, bioconversion, or catalytical systems, where a small acidic or alkaline component is continuously produced (e.g. lactate, acetate, ammonia, nitrate). By exchanging produced organic acid ions for hydroxide ions from an alkaline dialysate solution, which then neutralize the accompanying hydrogen ions, the overall result is a constant pH and significantly reduced accumulation of organic acid level. The case is similar for alkaline forming systems, where the alkaline ions are exchanged for hydrogen ions from an acidic dialysate, which in turn neutralize the hydroxide ions in the feed solution. In biological systems where the produced acids or alkalis act as growth inhibitors, the REED system's pH control is preferable to the standard pH titration control directly into the biological system, which only maintains pH level, but in itself is unable to suppress the build-up of neutralized acidic or alkaline metabolites.

In an embodiment of the invention the electrical field within any one REED stack is reversed asynchronically relative to any other REED membrane stack in the case of multiple either AX-REED or CX-REED membrane stacks.

The previously described short-term effect following each current reversal impacts the REED system's pH control by introducing a short-term negative effect until the membranes' ion profiles are re-established. In the case of AX-REED, acidic ions are extracted through one anion-exchange membrane in each feed compartment, while hydroxide ions enter through the opposite anion-exchange membrane. When the direction of the electrical current is reversed, the extracted acidic ions inside the first mentioned membrane is pushed back into the feed solution, before hydroxide ions starts entering the feed solution. Thus, in the short time period until the hydroxide profile is re-established through the membrane, which was previously used to extract acidic ions, no pH control is observed. The length of the time phase after each current reversal until pH control is regenerated depends on various process conditions and membrane properties; typically, it takes between 10-90 seconds before the process is again operating at complete pH control. This is registered as a sudden change in pH, which must then be regulated back to the desired set-point. In systems with more than one membrane stack, it is advantageous to perform the current reversals on each separate stack asynchronically, to spread out the instability effects and reduce the overall impact of current reversals. The use of asynchronical current reversal is disclosed in more detail in Applicant's copending patent application entitled "Method and system for improved process parameter control of a liquid composition in a reverse electro-enhanced dialysis (REED) system" of same date, which patent application is hereby incorporated by reference.

The interval length between current reversals for a stack is typically chosen with regard to the build-up of membrane fouling. Typically, said intervals within any one REED stack may be in the range 5-6000 seconds, preferably 8-3000 seconds, more preferably 10-2000 seconds and even more preferably 100-1500 seconds.

In an embodiment of the process according to the invention said at least one REED step comprises an Anion Exchange Reverse Electro-Enhanced Dialysis (AX-REED) step and said at least one step for controlling the level of target ions comprises a Cation-exchange Reverse Electro-Enhanced Dialysis (CX-REED) step.

In another embodiment of the process according to the invention said Reverse Electro-Enhanced Dialysis (REED) membrane stack is an Cation Exchange Reverse Electro-Enhanced Dialysis (CX-REED) stack and said at least one step for controlling the level of target ions comprises passing said liquid composition through a Anion Exchange Reverse Electro-Enhanced Dialysis (AX-REED) membrane stack.

The present invention provides advantages when combining AX-REED and CX-REED systems for improved control of pH and the level of target ions. It has previously been described how the REED process can be utilized for pH control and maintaining low level of inhibitors in bioprocesses, producing target ions in the form of low-molecular, charged inhibitors, e.g. organic acids or bases. In some systems, improved control of the level of target ions compared to what is achieved by the REED system's pH control is necessary.

To maintain a stable pH in a reactor producing target ions, a REED system used for pH control, in the following denoted the "Primary REED system", is regulated to neutralize the produced amount of acid or base ions in the reactor. To ensure this, a corresponding amount of either negatively charged or positively charged ions in the reactor is replaced by hydroxide or hydrogen ions, respectively. The ions replaced through this Primary REED system is a diverse representation of the either negatively charged or positively charged, low-molecular ions present in the reactor in question, and include the target ions. The distribution is determined by the ions's transport numbers, which numbers depend on molecular charge, ionic mobility, and concentration. When the REED pH control is typically operated on reactors with significant concentration of target ions, the main body of ions extracted and replaced as part of the pH controlling step typically constitutes target ions, thus assisting in maintaining a stable level of target ions below the inhibition level. When the REED is utilized for pH control in reactor systems with a high content of other ions (e.g. inorganic ions, amino acids), which resembles the target ions regarding charge and size, a reduced fraction of the ions replaced to maintain pH control constitute target ions. This causes a net accumulation of neutralized target ions in the pH controlled reactor.

In an embodiment of the invention a "Secondary REED system", which exchanges ions of opposite charge compared to the primary REED system is thus introduced for improved control of the level of target ions. In an acid-producing process, an AX-REED is used as Primary REED system for pH control to neutralize the acidic target ions. By adding a CX-REED as Secondary REED system, either in parallel or serial mode, cations from the reactor can be exchanged for hydrogen ions, which act as acidification of the reactor without adding more acid molecules. The pH regulating AX-REED will react to the increasing acidification by increasing the exchange of reactor anions for hydroxide ions, thus increasing the extraction of acidic target ions and overcoming any accumulation thereof, which could otherwise occur. It is then possible to reduce the concentration of target ions without upsetting the reactor's pH stability.

For alkali-producing processes, the principle is similar, using a CX-REED as Primary REED system for pH control, and an AX-REED for Secondary REED system for controlling the level of target ions.

Other process effects impact the reactor's overall concentration levels. Water is also exchanged through osmosis and electro-osmosis across the ion-exchange membranes in the REED system. When the ionic activity of dialysate is higher than the ionic activity of the reactor, as is typically the case, osmosis causes water molecules to diffuse from the reactor to the dialysate in the REED. When exchanging target ions with lower ionic mobility compared to the mobility of hydroxide or hydrogen ions, which replace them, an electro-osmotic flux of water molecules from the reactor into the dialysate is typically observed. Overall, the REED system typically extracts water from the reactor.

In an embodiment of the invention said Reverse Electro-Enhanced Dialysis (REED) membrane stack is an Anion Exchange Reverse Electro-Enhanced Dialysis (AX-REED) stack and said at least one step for controlling the level of target ions comprises a titration of said liquid with acid.

In an alternative embodiment of the invention said Reverse Electro-Enhanced Dialysis (REED) membrane stack is a Cation Exchange Reverse Electro-Enhanced Dialysis (CX- REED) stack and said at least one step for controlling the level of target ions comprises a titration of said liquid with alkali.

Addition of a non-inhibiting acid or base to the reactor will cause the Primary REED system to increase the ion-exchange causing the concentration of the inhibiting ion to decrease while the concentration of the non-inhibiting ion will increase. The concentration ratio between the two types of ions will approach an equilibrium value that depends on the ratio between the addition and formation rate of the inhibiting ion. In a specific embodiment the lactate concentration in a bioreactor is measured online and titration with a strong acid such as phosphoric acid is increased if the lactate concentration increases above a given set-point.

In an alternative embodiment of the invention said at least one step for controlling the level of target ions comprises addition of water to the reactor. Addition of volume, e.g. sterile water or more diluted feed components, will counter accumulation of target ions, but is limited by the reactor size or necessitates purge of excess volume. In a specific embodiment the conductivity in a bioreactor is measured online and addition of water is increased if the conductivity increases above a given set-point.

In an embodiment of the invention said at least one step for controlling the level of target ions comprises a filtration step, preferably a micro- or ultrafiltration step. Thus the use of perfusion systems, where the bioreactor's ferment is filtered through a pressure-driven membrane process, and continuously fed fresh substrate solution, allows for precise control of inhibitor level, e.g. through online concentration measurement or conductivity measurement.

In an embodiment of the invention the intensity of the applied electric field is adjusted in response to the pH, target ion concentration or conductivity of said liquid composition. By increasing the intensity of the electric field, the ion exchange increases in the REED system, and vice versa. Online, semi-online (e.g. time-delayed) or secondary (e.g. using online conductivity or turbidity measurements for estimating target ion concentration) measurements of the process parameters being regulated are input in a control regulation mechanism e.g. PID-control software, which in turn regulates the output of the power supplies to the REED electrodes.

In an embodiment of the invention said liquid composition is a fermentation mixture comprising immobilised or suspended microbial cultures or is an enzyme-containing mixture.

In an embodiment of the invention said microbial cultures comprise growing or resting cultures of bacteria, yeast, fungi or mammalian cells.

Another embodiment of the invention is a system comprising:
a) at least one Anion Exchange Reverse Electro-Enhanced Dialysis (AX-REED) membrane stack having:
   i. at least two Anion-exchange membranes defining a first chamber for a first liquid there between;
   ii. at least two further chambers for a second liquid, each further chamber being located adjacent to the at least one first chamber;
   iii. a set of end membranes; and
   iv. means for applying an electric field over the membranes by means of at least two electrodes; and
b) at least one Cation Exchange Reverse Electro-Enhanced Dialysis (CX-REED) membrane stack having
   v. at least two Cation-exchange membranes defining a third chamber for a third liquid there between;
   vi. at least two further chambers for a fourth liquid, each further chamber being located adjacent to the at least one third chamber;
   vii. a set of end membranes; and
   viii. means for applying an electric field over the membranes by means of at least two electrodes;
wherein said at least one Anion Exchange Reverse Electro-Enhanced Dialysis (AX-REED) membrane stack and said at least one Cation Exchange Reverse Electro-Enhanced Dialysis (CX-REED) membrane stack are in serial or parallel connection.

For a bioreactor fermenting by an organic acid-inhibited cell strain, an Anion Exchange REED (AX-REED) serves to replace produced organic acids with hydroxide ions, and thus, countering the reduction of pH from the acid-formation. By regulation of the AX-REED, the hydroxide exchange can maintain bioreactor pH without the need for neutralizer addition. Combining the AX-REED with a Cation Exchange REED (CX-REED) system, which exchanges cations in the bioreactor for e.g. hydrogen ions, it is possible to regulate the level of organic acid inhibitor as well as bioreactor pH.

The combined AX-REED and CX-REED offers the possibility of increased bioreactor control and, at the same time, reduces the need for adding neutraliser. The result is a bioreactor product with highly reduced salt levels, and significantly increased productivity since the cell growth is no longer limited by acid inhibition.

By operating the Primary and Secondary REED systems in parallel mode the time the ferment spends outside the bioreactor can be minimized. Since the optimal growth conditions are present inside the bioreactor, it is preferable that the ferment flows through the external REED system for as short a period as possible.

For optimal reactor control it is necessary to control the dialysate concentration and flow as well as temperature and mode of operation. The rate of ion exchange in the REED depends on a combination of electrical current and passive diffusion. The rate of diffusion depends on the concentration of the ion to be transferred from the dialysate into the reactor. If the dialysate has a high concentration of the pH regulating ion, e.g. hydroxide when AX-REED is the primary system, there will be a substantial diffusion of hydroxide into the reactor circuit regardless of the electrical current. It is therefore important to be able to control the concentration of the dialysate so that the rate of diffusion never exceeds the production rate in the reactor. This is done by linking the concentration and/or flow rate of dialysate to the electrical current output to the REED stacks so an increase in current will cause the concentration of dialysate to increase. Control of dialysate concentration can e.g. be carried out be regulating addition of water and concentrated dialysate solution into the dialysate stream prior to its entry in the REED system. Control of dialysate flow can e.g. be carried out by regulating the dialysate flow pump or using flow regulation valves.

In serial mode, it is possible to avoid that the ferment becomes either too acidic or too alkaline, which need be addressed if some components exhibit pH instabilities. Depending on the type of REED system, the ferment leaving a REED system has either been acidified or become more alkaline and then returns to normal pH, when remixed into the bioreactor. In a serial setup, it is possible to choose whether to start by increasing or reducing the ferment's pH by placing the appropriate REED system as the first step in the circulation loop outside the bioreactor in cases where pH instability is an issue.

It is possible to operate the dialysate flow in single pass mode, in batch mode, or a combination hereof depending on the production rate in the bioreactor. If low capacity is required, e.g. in the beginning of a fermentation process where the cell density is low, it is advantageous to circulate the dialysate over a tank. As productivity of the bioreactor increases an increasing percentage of the dialysate leaving the REED stack is discarded. When the process is running at full capacity all dialysate is discarded after a single pass through the stack and fresh dialysate is pumped into the stack. If multiple stacks are used it is possible to set up the dialysate flow either in parallel, or in serial with or without booster pumps between stacks.

The invention will now be described in further details in the following non-limiting specific examples.

EXAMPLES

Example 1

Figure 1:
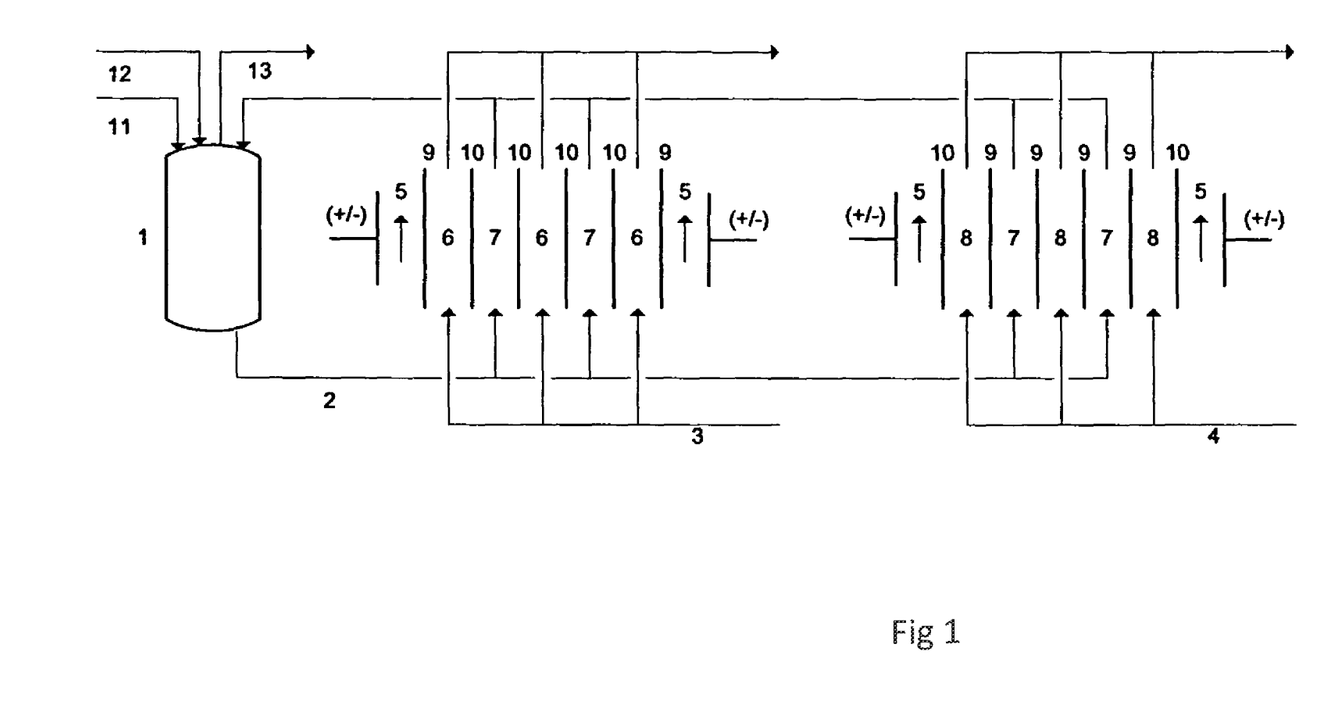
FIG. 1 shows a process setup with a combination of AX-REED and CX-REED connected to a bioreactor in parallel.

For expression of a certain active pharmaceutical ingredient (API), the lactic acid producing strain *Lactococcus Lactis* was cultivated using nutrient rich media in a 100 L bioreactor with both AX-REED and CX-REED connected in a setup as shown in FIG. 1. From the Bioreactor (1) the broth was pumped through interconnecting pipes (2) to the Ferment compartments (7) of both AX-REED and CX-REED before returning to the Bioreactor. In the dialysate compartments (6) of the AX-REED a solution of NaOH was pumped and in the dialysate compartments (8) of the CX-REED a solution of $HNO_3$ was pumped. The electrodes were rinsed by pumping a 0.5 M NaOH solution in the electrode compartments (5). The AX-REED comprised 2 membrane stacks with 50 cell pairs with a total active membrane area of 5.6 $m^2$. The single CX-REED stack connected to the loop was equipped with 20 cell pairs having a total membrane area of 1.1 $m^2$. The installed membranes was ASM anion exchange membranes (10) and CMXsb cation exchange membranes (9) both from ASTOM, Japan. A highly concentrated substrate solution was continuously added through a port (11) in the fermenter to maintain a specific glucose level and supply essential growth components. The wet weight of biomass was measured and adjusted by addition of sterile water (12) to the fermenter and excess volume with the API was harvested through a pipe (13) placed near the top of the fermenter.

Figure 2:
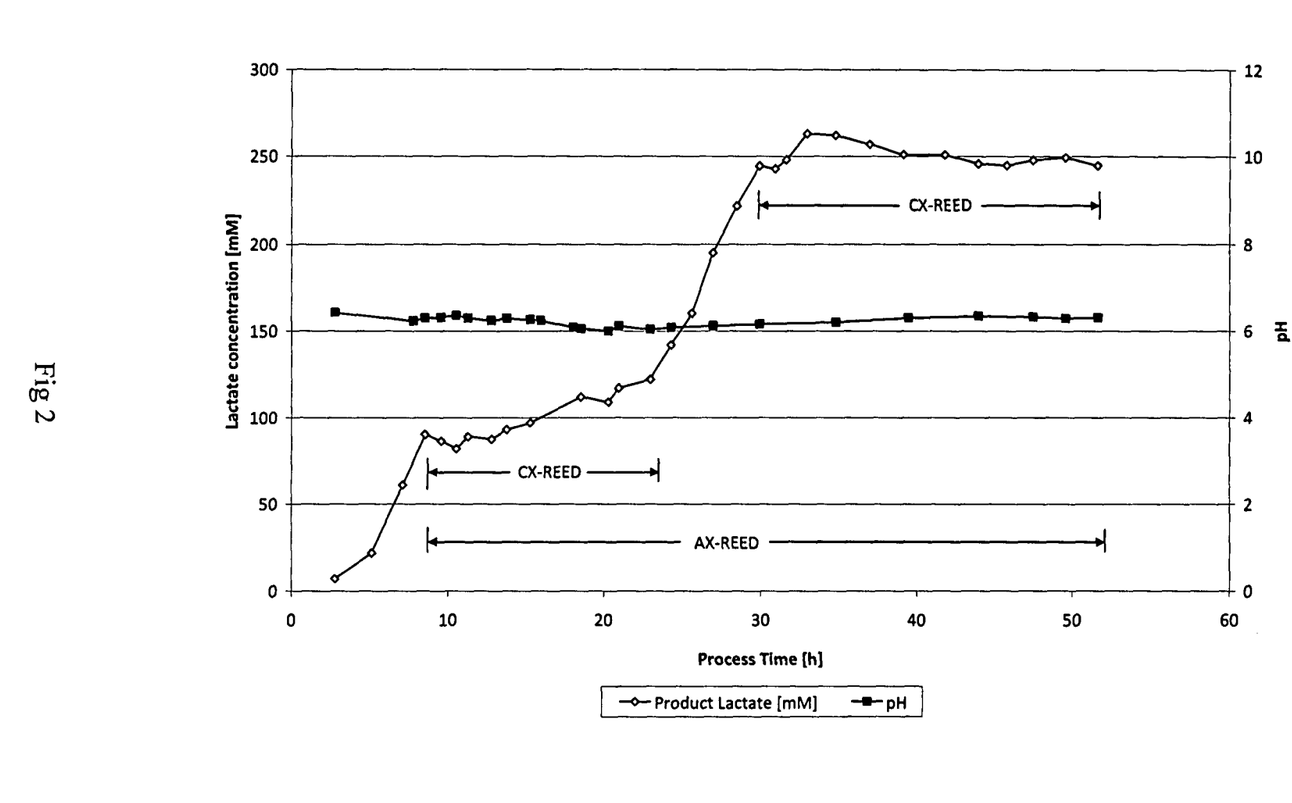
FIG. 2 shows the control of pH and lactate concentration using a combination of AX- and CX-REED.

The biomass is best generated at relatively low lactate concentration, but the expression of the API is optimal at a lactate concentration around 250 mM. Consequently, it is important to be able to maintain control of lactate levels throughout the fermentation. Both AX- and CX-REED was started 8 hours after inoculation of the fermenter at a lactate concentration of approx. 90 mM, see FIG. 2. Electrical current on the two AX-REED stacks was controlled to maintain a pH set-point of 6. A slight deviation from the set-point can be observed due to the pH probe for controlling the process being placed in the loop on the REED pilot rig rather than in the fermenter. The pH shown in FIG. 2 is the fermenter pH. Electrical current on the CX-REED stack was controlled to maintain a given conductivity, which was correlated to the lactate concentration. After 24 h the biomass concentration had reached the desired level and induction of the API expression system was gradually initiated. This was done by turning off the CX-REED and hereby let the lactate concentration increase to 250 mM before starting the CX-REED again after 30 h. After 52 h the fermentation was terminated and approx. 200 L broth (purge volume included) were collected for further purification.

The possibility to operate the fermentation at predetermined lactate levels boosted the API concentration with a factor of 10 compared to the standard batch fermentation.

Example 2

A similar setup as the one of Example 1 was used, however by addition of water to the fermenter. It was observed that addition of water to the fermenter reduced the need for electrical current on the CX REED stack. By suitable control of the water addition the CX REED could be omitted.

Example 3

This example demonstrates how a REED stack used for controlling one process parameter can be combined with addition of water for simultaneous control of a secondary process parameter in a simulated fed-batch fermentation process.

A parallel combination of an AX-REED with 10 cell pairs of 915 $cm^2$ each and a CX-REED with 2 cell pairs of 915 $cm^2$ each was connected to a 20 liter fermenter in a setup as shown in FIG. 1. The AX-REED and CX-REED were fitted with Neosepta AMS anion-exchange membranes (10) and Nafion N117 cation-exchange membranes (9). The membranes were fitted in JS-9 stacks (Jurag Separation, Denmark). The bioreactor/fermenter (1) was prepared to simulate a fed-batch fermentation with a 20 L model solution consisting of a phosphate buffer (60 mM) and sodium lactate (85 mM) at a pH of 6.5. To simulate the presence of a microorganism producing a target ion at a constant rate, 90% (w/w) lactic acid was added (11) at a rate of 75 ml/h, causing constant acidification. To simulate addition of nutritional components and presence of competitive ions, 5 M sodium chloride solution was continuously added (11) at a rate of 75 ml/h, causing constant build-up in salinity and fermenter conductivity. Fermenter temperature was maintained at 25° C.

Figure 3:
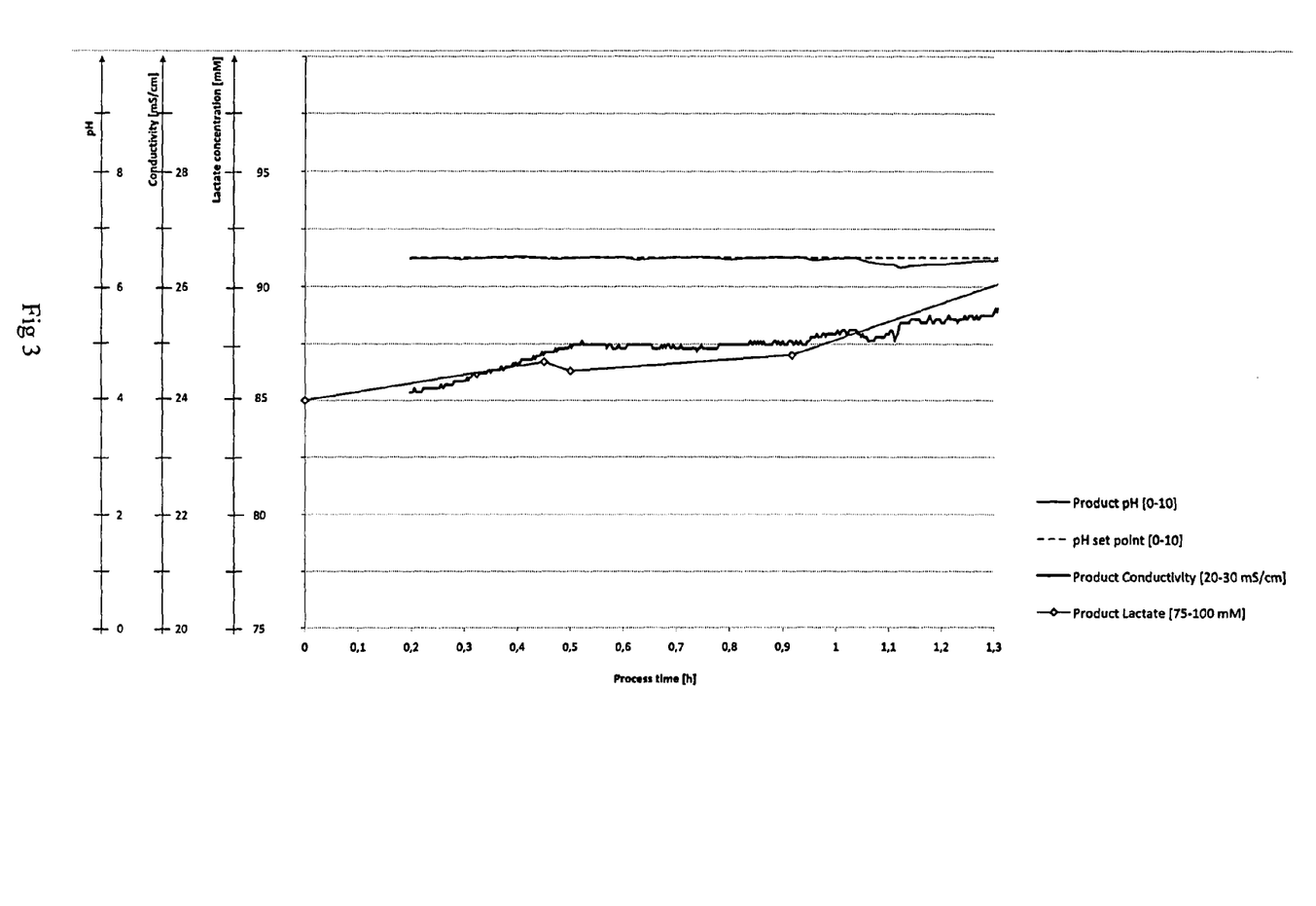
FIG. 3 shows the control of pH and lactate concentration using a combination of an AX-REED and a CX-REED connected to a bioreactor in parallel, where the AX-REED is active and the CX-REED is inactive.

The model solution in the fermenter was circulated (2) through the AX-REED and CX-REED in parallel and back to the fermenter. In the AX-REED unit, a dialysate solution (3) of 10 L 0.2M sodium hydroxide was circulated together with an electrode rinse solution (5) of 0.5M sodium hydroxide. The CX-REED was not active in this example and only deionized water was used for dialysate (4) in this unit. FIG. 3 shows the results from this example.

The AX-REED was used for pH regulation in the fermenter to a set-point of pH 6.5, by regulating the electrical field and addition of fresh sodium hydroxide to the AX-dialysate as controlled by a programmable logic controller (PLC) in accordance with a pH sensor in the fermenter. It was observed how the AX-REED negated the acidification from the lactic acid addition, but conductivity and concentration of target ion (lactate) still increased in the fermenter.

At a certain time (0.5 hours), deionized water was added (12) to the fermenter at the rate of 48 ml/h, which diluted the fermenter. The dilution controlled the conductivity of the fermenter to a constant value and reduced the accumulation of target ion (lactate) in the fermenter, while the AX-REED still controlled the fermenter pH. After 1 liter water was added to the fermenter, water addition was stopped, and renewed increase in conductivity and target ion was observed. The fermenter volume had increased from 20 to 21 L, as expected.

Example 4

This example demonstrates how a REED stack used for controlling one process parameter can be combined with a REED stack of opposite charge selectivity for simultaneous control of a secondary process parameter in a simulated fed-batch fermentation process.

The exact same setup was used as shown in FIG. 1 and described in example 3, combining an AX-REED and CX-REED. The same process parameters and solutions were employed as described in example 3. The only significant difference was that the CX-REED was active in part of this trial.

Figure 4:
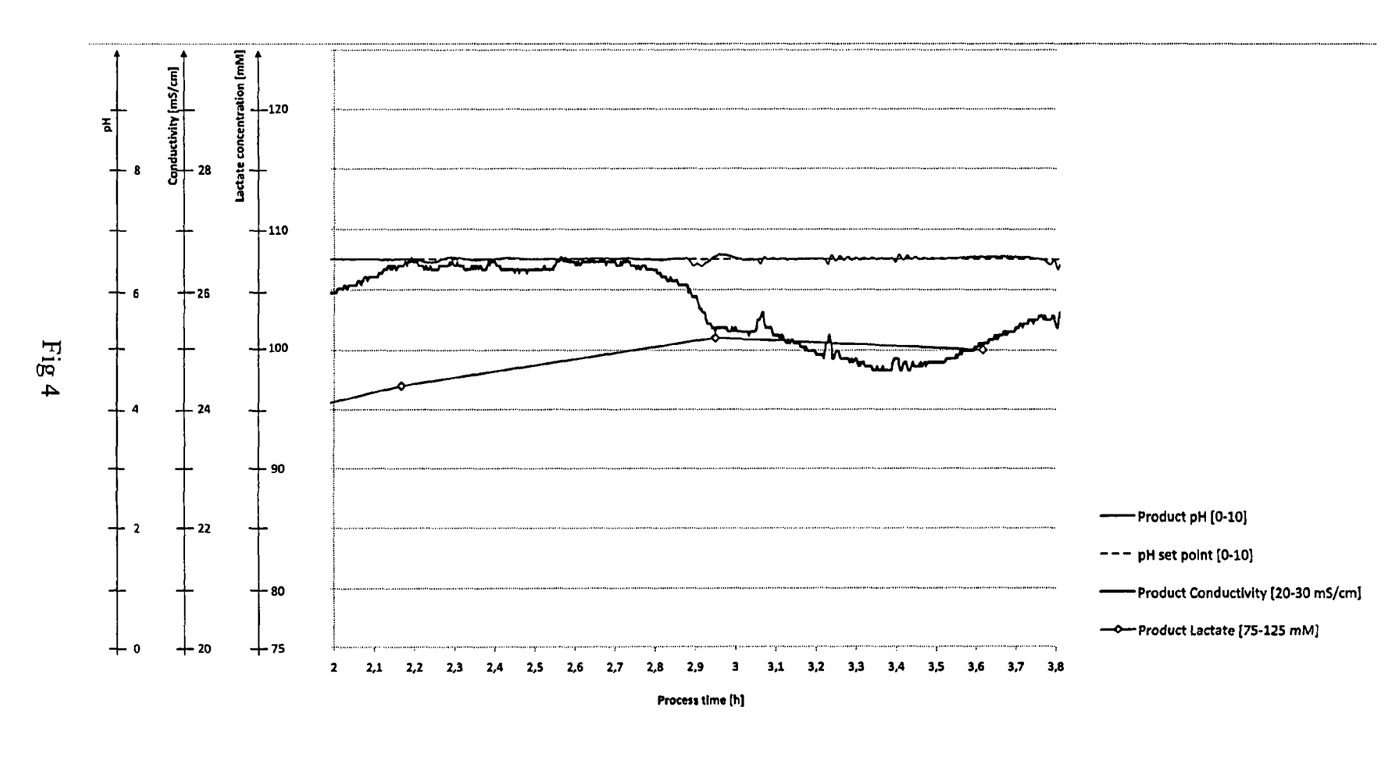
FIG. 4 shows the control of pH and lactate concentration using a combination of an AX-REED and a CX-REED connected to a bioreactor in parallel, where both the AX-REED and the CX-REED are active.

As in example 3 the fermenter started with 20 liter 60 mM phosphate buffer solution with 85 mM sodium lactate and addition of 90%(w/w) lactic acid (75 ml/h) and 5 M sodium chloride (75 ml/h). The solution circulated through the AX-REED and CX-REED units in parallel. FIG. 4 shows the results from this trial.

pH in the fermenter was controlled by the AX-REED as described in example 3, while conductivity and target ion (lactate) concentration increased. At a certain time (2.1 hours) into the trial, a dialysate solution consisting of 5 liter 0.05M nitric acid was circulated through the CX-REED (4). By regulating the electrical field in the CX-REED and adding fresh 0.05 M nitric acid to the CX-dialysate controlled by a programmable logic controller (PLC), the CX-REED controlled the conductivity of the fermenter to a fixed set-point while the AX-REED still controlled the pH parameter. By reducing the value of the conductivity set-point at a certain time (2.7 hours) of the process, the CX-REED was also able to reduce the fermenter conductivity according to the new, lower conductivity set-point, while pH was maintained.

After 2.9 hours of process time, the CX-REED electrical field was increased further, at it was observed that it was possible to reduce the accumulation and maintain the level of target ions (lactate), while the AX-REED was still regulated for stable fermenter pH.

Example 5

This example demonstrates how a REED stack used for controlling one process parameter can be combined with addition of acid for simultaneous control of a secondary process parameter in a simulated fed-batch fermentation process.

The exact same setup was used as shown in FIG. 1 and described in example 3, combining an AX-REED and CX-REED.

The same process parameters and solutions were employed as described in example 3.

Figure 5:
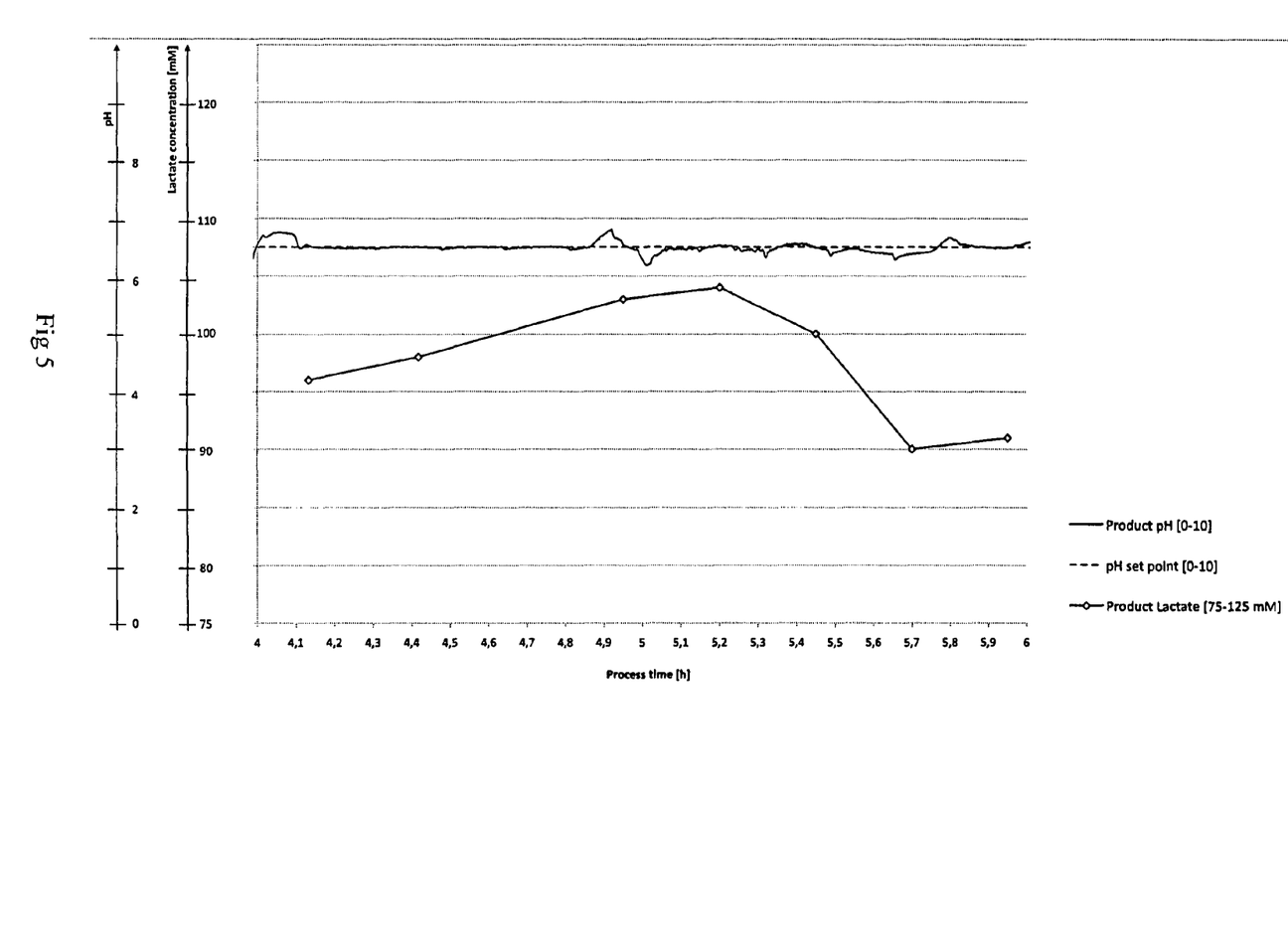
FIG. 5 shows the control of pH and lactate concentration using a combination of an AX-REED and a CX-REED connected to a bioreactor in parallel, where the AX-REED is active and the CX-REED is inactive.

As in example 3 the fermenter started with 20 liter 60 mM phosphate buffer solution with 85 mM sodium lactate, and addition of 90%(w/w) lactic acid (75 ml/h) and 5 M sodium chloride (75 ml/h). The solution circulated through the AX-REED and CX-REED units in parallel. FIG. 5 shows the results from this trial.

The CX-REED was not active in this example and only deionized water was used for dialysate (4) in this unit. pH in the fermenter was controlled by the AX-REED as described in example 3, while conductivity and target ion (lactate) concentration increased.

After 5 hours of process time, addition of 7.5 M phosphoric acid at a rate of 120 ml/h was started (12). For the AX-REED to continuously control fermenter pH, which was now affected by a combination of lactic acid addition and phosphoric acid addition, the AX-REED automatically reacted by increasing the exchange of hydroxide for lactate and other anions from the fermenter. Thus, it was seen to reduce the accumulation of target ions. At 5.2 hours of process time, the acid addition rate was increased to 300 ml/h, which resulted in a significant reduction in target ion (lactate) concentration, while the AX-REED, though working to neutralise two acidification effects, still controlled fermenter pH.

Example 6

A 150 L fed-batch fermentation tank was connected through tubes and a pump to a rig mounted with 5 AX-REED stacks and 1 CX-REED stack, all in a parallel setup. Each REED stack was a JS-9 stack (Jurag Separation, Denmark). The 5 AX-REED stacks held 54 cell pairs each while the CX-REED stack held 20 cell pairs; each cell pair has 915 $cm^2$ of active membrane area.

Figure 6:
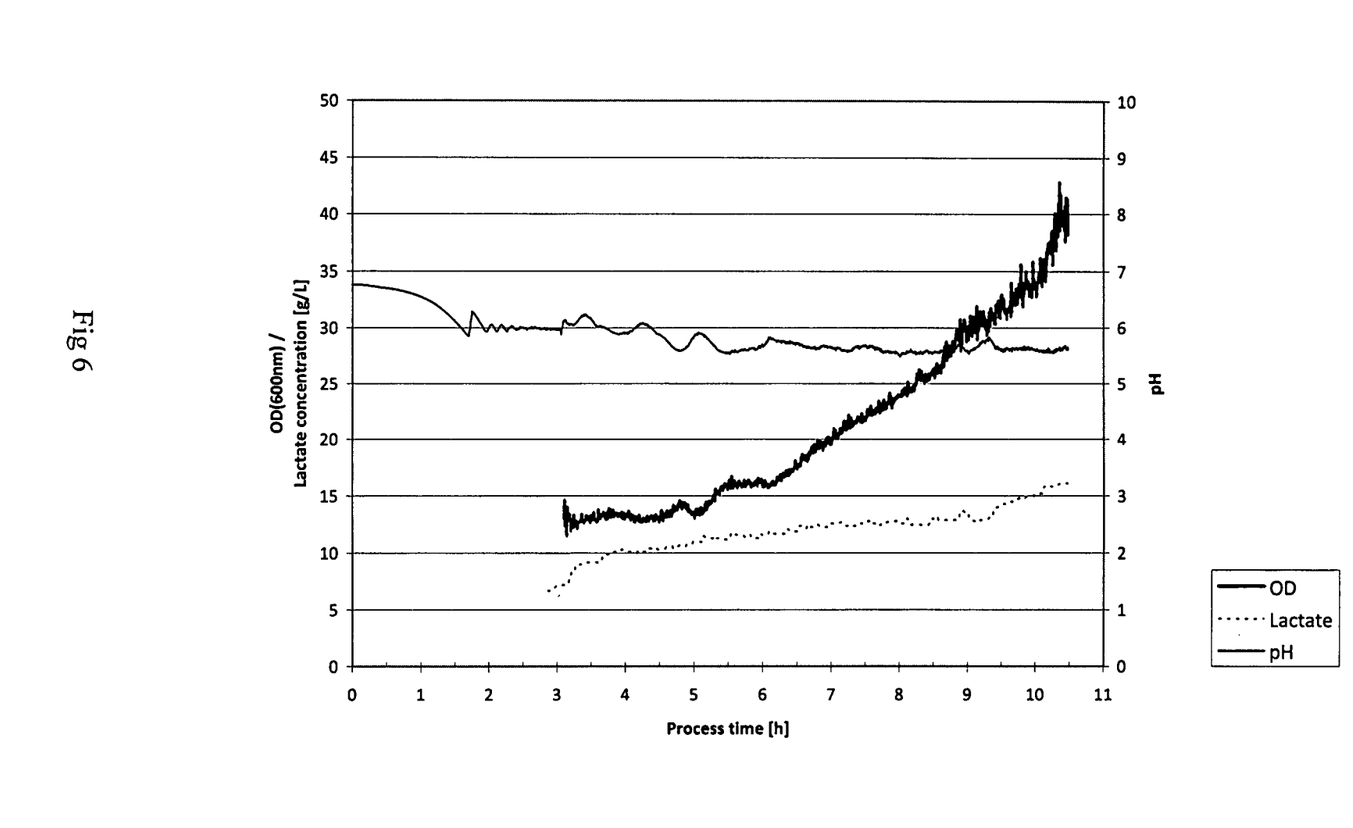
FIG. 6 shows the control of pH and lactate concentration using a combination of an AX-REED and a CX-REED connected to a bioreactor in parallel, where both the AX-REED and the CX-REED are active.

FIG. 6 shows the result of a REED-controlled fermentation. 150 L fermentation medium was transferred to the fermenter and inoculated by a lactic acid-producing cell strain. After 3 hours of process time with standard alkaline titration used for pH control in the fermenter, lactate concentration reached a predetermined level. Ferment then started to circulate between fermenter and REED stacks. pH control was transferred to the AX-REED stacks while CX-REED was used for control of target ion (lactate) regulation. After 4.5 hours of process time, the pH set-point was lowered to 5.6. After 9.5 hours of process time, the CX-REED control was reduced, which resulted in increasing lactate accumulation for the remainder of the fermentation.

pH and OD (Optical Density) was measured online in the fermenter by probes, while lactate concentration was sampled every two minutes.

FIG. 6 shows how the 5 AX-REED stacks maintained the fermenter pH, while the CX-REED, operating a near maximum capacity, kept lactate accumulation to a minimum. The OD (Optical Density) curve of FIG. 6 shows how the microorganisms maintained growth during the process.

The invention claimed is:

1. A process for simultaneously controlling the pH and the level of target ions of a liquid composition in an ongoing fermentation, where an acidic component is continuously produced and where said target ions are the ionic species of said acidic component, comprising at least one step of passing said liquid composition through at least one primary Reverse Electro-Enhanced Dialysis (REED) membrane stack, wherein each of the at least one primary REED membrane stack is an Anion Reverse Electro-Enhanced Dialysis (AX-REED) membrane stack, wherein said at least one step controls the pH in said liquid composition, and further comprising at least one further step of passing said liquid composition through at least one secondary Reverse Electro-Enhanced Dialysis (REED) membrane stack, wherein each of the at least one secondary REED membrane stack is a Cation Reverse Electro-Enhanced Dialysis (CX-REED) membrane stack, whereby at least some of said target ions are removed from said liquid composition, wherein said at least one further step controls the levels of target ions, wherein at least some of said primary REED stacks and some of said secondary REED stacks are operated in parallel, and wherein each said REED membrane stack has:

i) a set of end membranes;

ii) means for applying an electric field over the membranes by means of at least two electrodes of opposite polarity, wherein said at least two electrodes are located in at least two electrode chambers, said electrode chambers being located at each end of the apparatus and being bound by the end membranes;

iii) a first chamber for a first liquid therein, said first liquid being a dialysate liquid or said liquid composition; and iv) an even number of additional chambers arranged symmetrically around said first chamber; said additional chambers being for said dialysate liquid or for said liquid composition therein;
and wherein:
no two adjacent chambers contain the same liquid;
each of said first or additional chambers is defined by two ion exchange-membranes, wherein each of said ion-exchange membranes is of a first ionic type if it is in contact with two chambers and of a second ionic type identical to or different from said first ionic type if it is in contact with only one chamber; and
if the REED membrane stack is an AX-REED membrane stack, said first ionic type is anionic, and if the REED membrane stack is a CX-REED membrane stack, said first ionic type is cationic.

2. The process according to claim 1, wherein the polarity of said at least two electrodes is changed at intervals.

3. A process for simultaneously controlling the pH and the level of target ions of a liquid composition in an ongoing fermentation, where an alkaline component is continuously produced and where said target ions are the ionic species of said alkaline component, comprising at least one step of passing said liquid composition through at least one primary Exchange Reverse Electro-Enhanced Dialysis (REED) membrane stack, wherein each of the at least one primary REED membrane stack is a Cation Reverse Electro-Enhanced Dialysis (CX-REED) membrane stack, wherein said at least one step controls the pH in said liquid composition,
and further comprising at least one further step of passing said liquid composition through at least one secondary Reverse Electro-Enhanced Dialysis (REED) membrane stack, wherein each of the at least one secondary REED membrane stack is an Anion Reverse Electro-Enhanced Dialysis (AX-REED) membrane stack,
whereby at least some of said target ions are removed from said liquid composition,
wherein said at least one further step controls the levels of target ions,
wherein at least some of said primary REED stacks and some of said secondary REED stacks are operated in parallel,
and wherein each said REED membrane stack has:
i) a set of end membranes;
ii) means for applying an electric field over the membranes by means of at least two electrodes of opposite polarity, wherein said at least two electrodes are located in at least two electrode chambers, said electrode chambers being located at each end of the apparatus and being bound by the end membranes;
iii) a first chamber for a first liquid therein, said first liquid being a dialysate liquid or said liquid composition; and
iv) an even number of additional chambers arranged symmetrically around said first chamber; said additional chambers being for said dialysate liquid or for said liquid composition therein;
and wherein:
no two adjacent chambers contain the same liquid;
each of said first or additional chambers is defined by two ion exchange-membranes, wherein each of said ion-exchange membranes is of a first ionic type if it is in contact with two chambers and of a second ionic type identical to or different from said first ionic type if it is in contact with only one chamber; and
if the REED membrane stack is an AX-REED membrane stack, said first ionic type is anionic, and if the REED membrane stack is a CX-REED membrane stack, said first ionic type is cationic.

4. The process according to claim 1, wherein said step for controlling the level of target ions further comprises a filtration step.

5. The process according to claim 1, wherein the intensity of the applied electric field is adjusted in response to the pH, target ion concentration, or conductivity of said liquid composition.

6. The process according to claim 1, wherein said liquid composition is a fermentation mixture comprising immobilized or suspended microbial cultures or is an enzyme-containing mixture.

7. The process according to claim 6, wherein said microbial cultures comprise growing or resting cultures of bacteria, yeast, fungi or mammalian cells.

8. The process according to claim 6, wherein productivity and longevity of cell growth and/or metabolite production in a bioreactor/live fermentation process is improved by extracting inhibitors like organic acid ions.

9. A method for producing a liquid, said method involving use of a process for simultaneously controlling the pH and the level of target ions of a liquid composition in an ongoing fermentation, where an acidic component is continuously produced and where said target ions are the ionic species of said acidic component, comprising at least one step of passing said liquid composition through at least one primary Reverse Electro-Enhanced Dialysis (REED) membrane stack, wherein each of the at least one primary REED membrane stack is an Anion Reverse Electro-Enhanced Dialysis (AX-REED) membrane stack, wherein said at least one step controls the pH in said liquid composition,
and further comprising at least one further step of passing said liquid composition through at least one secondary Reverse Electro-Enhanced Dialysis (REED) membrane stack, wherein each of the at least one secondary REED membrane stack is a Cation Reverse Electro-Enhanced Dialysis (CX-REED) membrane stack,
whereby at least some of said target ions are removed from said liquid composition,
wherein said at least one further step controls the levels of target ions,
wherein at least some of said primary REED stacks and some of said secondary REED stacks are operated in parallel, and wherein each said REED membrane stack has:
i) a set of end membranes;
ii) means for applying an electric field over the membranes by means of at least two electrodes of opposite polarity, wherein said at least two electrodes are located in at least two electrode chambers, said electrode chambers being located at each end of the apparatus and being bound by the end membranes;
iii) a first chamber for a first liquid therein, said first liquid being a dialysate liquid or said liquid composition; and
iv) an even number of additional chambers arranged symmetrically around said first chamber; said additional chambers being for said dialysate liquid or for said liquid composition therein;
and wherein:
no two adjacent chambers contain the same liquid;
each of said first or additional chambers is defined by two ion exchange-membranes, wherein each of said ion-exchange membranes is of a first ionic type if it is in contact with two chambers and of a second ionic type identical to or different from said first ionic type if it is in contact with only one chamber; and
if the REED membrane stack is an AX-REED membrane stack, said first ionic type is anionic, and if the REED membrane stack is a CX-REED membrane stack, said first ionic type is cationic.

10. The method according to claim 9, wherein the liquid composition is a fermentation mixture comprising immobilized or suspended microbial cultures or is an enzyme-containing mixture.

11. A process for simultaneously controlling the pH and the level of target ions of a liquid composition in an ongoing catalytical system, where an acidic component is continuously produced and where said target ions are the ionic species of said acidic component, comprising at least one step of passing said liquid composition through at least one primary Reverse Electro-Enhanced Dialysis (REED) membrane stack, wherein each of the at least one primary REED membrane stack is an Anion Reverse Electro-Enhanced Dialysis (AX-REED) membrane stack, wherein said at least one step controls the pH in said liquid composition, and further comprising at least one further step of passing said liquid composition through at least one secondary Reverse Electro-Enhanced Dialysis (REED) membrane stack, wherein each of the at least one secondary REED membrane stack is a Cation Reverse Electro-Enhanced Dialysis (CX-REED) membrane stack, whereby at least some of said target ions are removed from said liquid composition, wherein said at least one further step controls the levels of target ions, wherein at least some of said primary REED stacks and some of said secondary REED stacks are operated in parallel, and wherein each said REED membrane stack has:
i) a set of end membranes;
ii) means for applying an electric field over the membranes by means of at least two electrodes of opposite polarity, wherein said at least two electrodes are located in at least two electrode chambers, said electrode chambers being located at each end of the apparatus and being bound by the end membranes;
iii) a first chamber for a first liquid therein, said first liquid being a dialysate liquid or said liquid composition; and
iv) an even number of additional chambers arranged symmetrically around said first chamber; said additional chambers being for said dialysate liquid or for said liquid composition therein;

and wherein:
no two adjacent chambers contain the same liquid;
each of said first or additional chambers is defined by two ion exchange-membranes, wherein each of said ion-exchange membranes is of a first ionic type if it is in contact with two chambers and of a second ionic type identical to or different from said first ionic type if it is in contact with only one chamber; and
if the REED membrane stack is an AX-REED membrane stack, said first ionic type is anionic, and if the REED membrane stack is a CX-REED membrane stack, said first ionic type is cationic.

12. A method for producing a liquid, said method involving use of a process for simultaneously controlling the pH and the level of target ions of a liquid composition in an ongoing catalytical system, where an acidic component is continuously produced and where said target ions are the ionic species of said acidic component, comprising at least one step of passing said liquid composition through at least one primary Reverse Electro-Enhanced Dialysis (REED) membrane stack, wherein each of the at least one primary REED membrane stack is an Anion Reverse Electro-Enhanced Dialysis (AX-REED) membrane stack, wherein said at least one step controls the pH in said liquid composition, and further comprising at least one further step of passing said liquid composition through at least one secondary Reverse Electro-Enhanced Dialysis (CREED) membrane stack, wherein each of the at least one secondary REED membrane stack is a Cation Reverse Electro-Enhanced Dialysis (CX-REED) membrane stack, whereby at least some of said target ions are removed from said liquid composition, wherein said at least one further step controls the levels of target ions, wherein at least some of said primary REED stacks and some of said secondary REED stacks are operated in parallel, and wherein each said REED membrane stack has:
i) a set of end membranes;
ii) means for applying an electric field over the membranes by means of at least two electrodes of opposite polarity, wherein said at least two electrodes are located in at least two electrode chambers, said electrode chambers being located at each end of the apparatus and being bound by the end membranes;
iii) a first chamber for a first liquid therein, said first liquid being a dialysate liquid or said liquid composition; and
iv) an even number of additional chambers arranged symmetrically around said first chamber; said additional chambers being for said dialysate liquid or for said liquid composition therein;

and wherein:
no two adjacent chambers contain the same liquid;
each of said first or additional chambers is defined by two ion exchange-membranes, wherein each of said ion-exchange membranes is of a first ionic type if it is in contact with two chambers and of a second ionic type identical to or different from said first ionic type if it is in contact with only one chamber; and
if the REED membrane stack is an AX-REED membrane stack, said first ionic type is anionic, and if the REED membrane stack is a CX-REED membrane stack, said first ionic type is cationic.

13. The process according to claim 11, wherein the polarity of said at least two electrodes is changed at intervals.

14. A method for producing a liquid, said method involving use of a process for simultaneously controlling the pH and the level of target ions of a liquid composition in an ongoing catalytical system, where an alkaline component is continuously produced and where said target ions are the ionic species of said alkaline component, comprising at least one step of passing said liquid composition through at least one primary Reverse Electro-Enhanced Dialysis (REED) membrane stack, wherein each of the at least one primary REED membrane stack is a Cation Reverse Electro-Enhanced Dialysis (CX-REED) membrane stack, wherein said at least one step controls the pH in said liquid composition, and further comprising at least one further step of passing said liquid composition through at least one secondary Reverse Electro-Enhanced Dialysis (REED) membrane stack, wherein each of the at least one secondary REED membrane stack is an Anion Reverse Electro-Enhanced Dialysis (AX-REED) membrane stack, whereby at least some of said target ions are removed from said liquid composition, wherein said at least one further step controls the levels of target ions, wherein at least some of said primary REED stacks and some of said secondary REED stacks are operated in parallel, and wherein each said REED membrane stack has:
i) a set of end membranes;
ii) means for applying an electric field over the membranes by means of at least two electrodes of opposite polarity, wherein said at least two electrodes are located in at least two electrode chambers, said electrode chambers being located at each end of the apparatus and being bound by the end membranes;
iii) a first chamber for a first liquid therein, said first liquid being a dialysate liquid or said liquid composition; and
iv) an even number of additional chambers arranged symmetrically around said first chamber; said additional chambers being for said dialysate liquid or for said liquid composition therein;

and wherein:
no two adjacent chambers contain the same liquid;
each of said first or additional chambers is defined by two ion exchange-membranes, wherein each of said ion-exchange membranes is of a first ionic type if it is in contact with two chambers and of a second ionic type identical to or different from said first ionic type if it is in contact with only one chamber; and
if the REED membrane stack is an AX-REED membrane stack, said first ionic type is anionic, and if the REED membrane stack is a CX-REED membrane stack, said first ionic type is cationic.

15. The process according to claim 11, wherein said step for controlling the level of target ions further comprises a filtration step.

16. The process according to claim 11, wherein the intensity of the applied electric field is adjusted in response to the pH, target ion concentration, or conductivity of said liquid composition.

17. The process according to claim 11, wherein said liquid composition is a fermentation mixture comprising immobilized or suspended microbial cultures or is an enzyme-containing mixture.

18. The method according to claim 12, wherein the liquid composition is a fermentation mixture comprising immobilized or suspended microbial cultures or is an enzyme-containing mixture.

19. A method for producing a liquid, said method involving use of a process for simultaneously controlling the pH and the level of target ions of a liquid composition in an ongoing fermentation, where an alkaline component is continuously produced and where said target ions are the ionic species of said alkaline component, comprising at least one step of passing said liquid composition through at least one primary Reverse Electro-Enhanced Dialysis (REED) membrane stack, wherein each of the at least one primary REED membrane stack is a Cation Reverse Electro-Enhanced Dialysis (CX-REED) membrane stack, wherein said at least one step controls the pH in said liquid composition,
and further comprising at least one further step of passing said liquid composition through at least one secondary Reverse Electro-Enhanced Dialysis (REED) membrane stack, wherein each of the at least one secondary REED membrane stack is an Anion Reverse Electro-Enhanced Dialysis (AX-REED) membrane stack,
whereby at least some of said target ions are removed from said liquid composition,
wherein said at least one further step controls the levels of target ions,
wherein at least some of said primary REED stacks and some of said secondary REED stacks are operated in parallel, and wherein each said REED membrane stack has:
i) a set of end membranes;
ii) means for applying an electric field over the membranes by means of at least two electrodes of opposite polarity, wherein said at least two electrodes are located in at least two electrode chambers, said electrode chambers being located at each end of the apparatus and being bound by the end membranes;
iii) a first chamber for a first liquid therein, said first liquid being a dialysate liquid or said liquid composition; and
iv) an even number of additional chambers arranged symmetrically around said first chamber; said additional chambers being for said dialysate liquid or for said liquid composition therein;

and wherein:
no two adjacent chambers contain the same liquid;
each of said first or additional chambers is defined by two ion exchange-membranes, wherein each of said ion-exchange membranes is of a first ionic type if it is in contact with two chambers and of a second ionic type identical to or different from said first ionic type if it is in contact with only one chamber; and
if the REED membrane stack is an AX-REED membrane stack, said first ionic type is anionic, and if the REED membrane stack is a CX-REED membrane stack, said first ionic type is cationic.

20. A process for simultaneously controlling the pH and the level of target ions of a liquid composition in an ongoing catalytical system, where an alkaline component is continuously produced and where said target ions are the ionic species of said alkaline component, comprising at least one step of passing said liquid composition through at least one primary Reverse Electro- Enhanced Dialysis (REED) membrane stack, wherein each of the at least one primary REED membrane stack is a Cation Reverse Electro-Enhanced Dialysis (CX-REED) membrane stack, wherein said at least one step controls the pH in said liquid composition,
and further comprising at least one further step of passing said liquid composition through at least one secondary Reverse Electro-Enhanced Dialysis (REED) membrane stack, wherein each of the at least one secondary REED membrane stack is an Anion Reverse Electro-Enhanced Dialysis (AX-REED) membrane stack,
whereby at least some of said target ions are removed from said liquid composition,
wherein said at least one further step controls the levels of target ions,
wherein at least some of said primary REED stacks and some of said secondary REED stacks are operated in parallel,
and wherein each said REED membrane stack has:
i) a set of end membranes;
ii) means for applying an electric field over the membranes by means of at least two electrodes of opposite polarity, wherein said at least two electrodes are located in at least two electrode chambers, said electrode chambers being located at each end of the apparatus and being bound by the end membranes;
iii) a first chamber for a first liquid therein, said first liquid being a dialysate liquid or said liquid composition; and
iv) an even number of additional chambers arranged symmetrically around said first chamber; said additional chambers being for said dialysate liquid or for said liquid composition therein;

and wherein:
- no two adjacent chambers contain the same liquid;
- each of said first or additional chambers is defined by two ion exchange-membranes, wherein each of said ion-exchange membranes is of a first ionic type if it is in contact with two chambers and of a second ionic type identical to or different from said first ionic type if it is in contact with only one chamber; and
- if the REED membrane stack is an AX-REED membrane stack, said first ionic type is anionic, and if the REED membrane stack is a CX-REED membrane stack, said first ionic type is cationic.

* * * * *